United States Patent [19]
Behringer et al.

[11] Patent Number: 5,910,594
[45] Date of Patent: Jun. 8, 1999

[54] PROCESS FOR THE MANUFACTURE OF 5-CYANO-4-LOWER ALKYL-OXAZOLES

[75] Inventors: Klaus Behringer, Basle, Switzerland; Werner Bonrath, Freiburg, Germany; Horst Pauling, Bottmingen, Switzerland

[73] Assignee: Roche Vitamins Inc., Parsippany, N.J.

[21] Appl. No.: 09/008,793

[22] Filed: Jan. 20, 1998

[30] Foreign Application Priority Data

Feb. 13, 1997 [EP] European Pat. Off. .............. 97102339

[51] Int. Cl.$^6$ ..................... C07D 263/34; C07D 263/30; C07D 263/44; C07D 263/36
[52] U.S. Cl. ............................................. 548/236
[58] Field of Search ............................................. 548/236

[56] References Cited

U.S. PATENT DOCUMENTS

| | | | |
|---|---|---|---|
| 3,222,374 | 12/1965 | Chase | 548/236 |
| 4,026,778 | 5/1977 | Lalonde et al. | 204/159 |
| 4,026,901 | 5/1977 | Coffen, I | 548/236 |
| 4,051,174 | 9/1977 | Stoller et al. | 560/234 |
| 4,093,654 | 6/1978 | Coffen, II | 548/236 X |
| 4,255,584 | 3/1981 | Hoffmann-Paquotte, I | 548/236 |
| 4,772,718 | 9/1988 | Nösberger, I | 548/236 |
| 5,214,162 | 5/1993 | Nösberger, II | 548/236 |
| 5,502,212 | 3/1996 | Bonrath et al. | 548/236 |

FOREIGN PATENT DOCUMENTS

| | | |
|---|---|---|
| 0 010 697 | 5/1980 | European Pat. Off. . |
| 770 604 | 5/1997 | European Pat. Off. . |

OTHER PUBLICATIONS

Cragg et al, Tetrahedron Letters, vol. 22, No. 22, pp. 2127 to 2130, 1981.

Fieser et al, "Reagents for Organic Synthesis", vol. 10, p. 347, 1982.

Rinderspacher et al, "Über Dipyridl–ähnliche Thiazolyl–oxazole", Helvetica Chimica Acta 43:1522–1530 (1960).

Tetrahedron Letters 19:1501–1502 (1971) Lehnert.

*Primary Examiner*—Floyd D. Higel
*Attorney, Agent, or Firm*—George W. Johnston; Dennis P. Tramaloni

[57] ABSTRACT

A process for the manufacture of a 5-cyano-4-lower alkyl-oxazole by the dehydration of a 5-carbamoyl-4-lower alkyl-oxazole is disclosed. The reaction is carried out by dehydrating the oxazole with silicon tetrachloride in the presence of an amine in an aprotic organic solvent. 5-Carbamoyl-4-methyl-oxazole may be dehydrated by the process in accordance with the invention to obtain 5-cyano-4-methyl-oxazole, which is a valuable intermediate in the synthesis of pyridoxine.

21 Claims, No Drawings

PROCESS FOR THE MANUFACTURE OF 5-CYANO-4-LOWER ALKYL-OXAZOLES

BACKGROUND OF THE INVENTION

The present invention is concerned with a novel process for the manufacture of 5-cyano-4-lower alkyl-oxazoles. These oxazoles form an important group of substances. For example, 5-cyano-4-methyl-oxazole is a valuable intermediate in the synthesis of pyridoxine (vitamin $B_6$).

Several processes for the manufacture of 5-cyano-4-methyl-oxazole by the dehydration of 5-carbamoyl-4-methyl-oxazole have already been described. Thus, this dehydration has been carried out, for example, in the presence of phosphorus pentoxide [see Helv. Chim. Acta 43, 1522–1530 (1960)]. The disadvantages of this process are, however, the low yield of product, which is presumably due to the carbonization which occurs very readily in this reaction, and the formation of phosphate byproduct which is considered to be a problematic waste product.

An improvement in this process is achieved by reacting 5-carbamoyl-4-methyl-oxazole with phosphorus pentoxide in the presence of quinoline as the solvent [U.S. Patent (U.S. Pat. No. ) 3,222,374]. However, this process also has disadvantages which result from the toxicity of the quinoline, its unpleasant smell as well as its thermal instability. Moreover, quinoline is a relatively expensive solvent. The regeneration of the quinoline, the required use of stoichiometric amounts of phosphorus pentoxide, the costly working-up of the byproducts of the phosphorus pentoxide (phosphates) as well as their disposal in an environmentally proper manner represent further problems.

Another known process for the manufacture of 5-cyano-4-methyl-oxazole comprises reacting 5-carbamoyl-4-methyl-oxazole with a lower alkanecarboxylic acid anhydride and subjecting the reaction mixture or the 4-methyl-5-(N-lower alkanoylcarbamoyl)-oxazole isolated therefrom to a pyrolysis [European Patent Publication (EP) 10 697]. However, the final pyrolytic step has certain disadvantages, especially corrosion problems which occur with the reactor materials and the formation of byproducts which are difficult to recycle. Further, the high temperature at which the pyrolysis must be effected is a disadvantage.

The process described in U.S. Pat. No. 4,026,901 comprises catalytically dehydrating 5-carbamoyl-4-methyl-oxazole while heating at a high temperature in the presence of phosphorus pentoxide on a solid carrier. Disadvantages in this process are the handling of 5-carbamoyl-4-methyl-oxazole, especially the sublimation which is of prime consideration and simultaneously the solid dosing of the low volatile starting material, as well as, moreover, the formation and the disposal in an environmentally proper manner of the phosphate byproduct.

Further, the one-step conversion of ethyl 4-methyl-oxazole-5-carboxylate into 5-cyano-4-methyl-oxazole is described in U.S. Pat. No. 4,772,718. In this process the corresponding oxazole ester is converted into 5-cyano-4-methyl-oxazole in the presence of ammonia and a zirconium oxide or hafnium oxide catalyst in the gas phase. Disadvantages here are, however, the use of a relatively expensive catalyst as well as—in order to achieve an optimum reaction control—the maintenance of very precise reaction conditions, inter alia an inconveniently high reaction temperature. The industrial cost is accordingly high.

The gas phase dehydration of 5-carbamoyl-4-methyl-oxazole to 5-cyano-4-methyloxazole described in EP 492 233 has the disadvantage that the conversion must be carried out at reaction temperatures of about 400° C. to about 500° C. and at a high pressure, viz. of about 50 to about 300 kPa. Moreover, a high industrial cost is involved.

A further process is disclosed in U.S. Pat. No. 5,502,212 where 5-carbamoyl-4-lower alkyloxazoles are dehydrated to the corresponding 5-cyano-4-lower alkyl-oxazoles by reaction of the starting material with an N,N-disubstituted formamide and cyanuric chloride in a polar, aprotic organic solvent.

A process for the preparation of nitriles from carboxamides at a low temperature is described in Tetrahedron Letters 19, 1501–1502 (1971). The dehydration is effected by reaction with a two-fold molar excess of titanium tetrachloride. No reference is made to the dehydration of oxazolecarboxamides or compounds of similar structure.

SUMMARY OF THE INVENTION

The object of the present invention is to provide a process for the manufacture of a 5-cyano-4-lower alkyl-oxazole by the dehydration of a 5-carbamoyl-4-lower-alkyl-oxazole which does not have the disadvantages of the previously known relevant prior art processes and by means of which the 5-cyano-4-lower alkyl-oxazole is obtained in a short reaction time, under mild reaction conditions and in high yield. The process in accordance with the invention comprises carrying out the dehydration with silicon tetrachloride in the presence of an amine and in an organic solvent. The silicon tetrachloride dehydrating agent used in accordance with the invention is relatively cost-effective and the silicon dioxide which accrues in the course of the dehydration does not pose environmental problems. Furthermore, the good recycling rates of the solvent and bases (amines) used are advantageous.

DETAILED DESCRIPTION OF THE INVENTION

The term "lower alkyl" signifies in the scope in the present invention a straight-chain or branched alkyl group with 1 to 6 carbon atoms, e.g., methyl, ethyl, propyl, isopropyl, butyl, isobutyl, tert.butyl, pentyl or hexyl. Straight-chain alkyl groups, especially methyl and ethyl, primarily methyl, are preferred.

The amine used in accordance with the present invention is not critical, so long as it is soluble in the solvent. Both aliphatic amines and nitrogen-containing heteroaromatic compounds are suitable as amines. Especially suitable aliphatic amines are the tertiary aliphatic amines, especially trialkylamines with straight-chain or branched alkyl groups containing 1 to 10 carbon atoms. Examples of such alkyl groups are methyl, ethyl, n-propyl, isopropyl, n-butyl, isobutyl, tert.butyl, pentyl, hexyl, octyl and decyl. In such trialkylamines, the alkyl groups can be the same or different. The preferred trialkylamines are triethylamine, diisopropylethylamine and tri(n-butyl)amine.

The nitrogen-containing heteroaromatic compounds are especially heterocycles in which the ring contains at least one nitrogen atom. Examples are pyridine and pyridine derivatives such as picoline and quinoline.

The solvent is not critical, and may be selected from a wide variety of aprotic organic solvents. Suitable organic solvents for the process in accordance with the invention are especially aliphatic and cyclic ethers, e.g., diethyl ether and tert.butyl methyl ether or, respectively, tetrahydrofuran and dioxan; aliphatic nitriles, e.g., acetonitrile; aromatic hydrocarbons, e.g., toluene; as well as N-methylpyrrolidone.

Preferably, tert.butyl methyl ether or acetonitrile is used as the solvent. The amount of solvent is not critical. Any amount which is sufficient to dissolve or disperse the reactants, which prevents an overly exothermic reaction, and which provides the desired fluidity of the reaction mixture may be used.

The temperature at which the process of the invention is carried out is not critical, so long as some dehydration occurs. Preferably, for the dehydration, the 5-carbamoyl-4-lower alkyl-oxazole is reacted with the silicon tetrachloride dehydrating agent at room temperature or higher temperatures up to about 65° C., more preferably at temperatures from about 25° C. to about 60° C., particularly from about 45° C. to about 55° C.

The order in which the reactants are mixed is not critical. The process in accordance with the invention is preferably carried out by adding the silicon tetrachloride dropwise to a well-stirred solution or suspension of the 5-carbamoyl-4-lower alkyl-oxazole and the amine in the solvent.

The ratio of reactants is not critical, so long as some dehydration occurs. The reaction with silicon tetrachloride is preferably effected using a silicon tetrachloride: 5-carbamoyl-4-lower alkyl-oxazole molar ratio from about 0.6:1 to about 3:1, more preferably from about 0.7:1 to about 0.75:1. The amine:5-carbamoyl-4-lower alkyloxazole molar ratio is preferably from about 2.1:1 to about 3.5:1, more preferably from about 2.7:1 to about 2.9:1. Depending on the solvent used, its amount compared with the amount of 5-carbamoyl-4-lower alkyl-oxazole (oxazole) used is preferably from about 500 to about 900 ml per mole of oxazole, more preferably from about 550 to about 650 ml per mole of oxazole. Moreover, although not critical, it is recommended to carry out the dehydration under an inert gas, e.g., argon or nitrogen, in order to exclude oxygen as far as possible. In this manner the dehydration has normally finished within about 4 to 10 hours, preferably within about 5 to 7 hours.

The working-up in order to isolate the 5-cyano-4-lower alkyl-oxazole can be effected by conventional procedures used in organic chemistry, e.g., by distillation.

As mentioned above, an advantage of the process in accordance with the invention is that the silicon dioxide which accrues in the course of the dehydration, the solvent as well as the amine can be recovered and recycled by conventional means after the reaction has been effected. Further, the yield of 5-cyano-4-lower alkyl-oxazole is high.

The following Examples illustrate the process in accordance with the invention.

EXAMPLE 1

General procedure for the dehydration of 5-carbamoyl-4-methyl-oxazole to 5-cyano-4-methyl-oxazole 2.52 g (20 mmol) of 5-carbamoyl-4-methyl-oxazole (OXA) were placed under argon in a 350 ml four-necked sulphonation flask fitted with a stirrer, cooled stirring jacket, thermometer, 50 ml dropping funnel (without pressure balance) and Dimroth condenser. Subsequently, 60–80 ml of a solvent and 60 mmol of an amine as the base were added. Thereafter, 22–60 mmol of silicon tetrachloride ($SiCl_4$) were added dropwise as the dehydrating agent to the suspension present while stirring well in such a manner that the internal temperature in the flask did not exceed 45° C. The dropwise addition took about 15 minutes. The batch was subsequently heated to 60° C., becoming reddish to very dark brown in colour.

The yield of 5-cyano-4-methyl-oxazole (OXN) was determined in each case by gas chromatography (GC) and the content determinations were effected in each case using an internal standard.

a) Use of different solvents

These experiments were carried out at 60° C. with 6.07 g (60 mmol) of triethylamine as the base and 4.4 g (26 mmol) of $SiCl_4$ as the dehydrating agent ($SiCl_4$:OXA molar ratio= 1.3:1). The reaction time was variously 2, 4 or 5 hours. The results of the experiments in which various solvents were used in an amount of 60 or 80 ml are compiled in the following Table 1. The yields of OXN were determined by GC.

TABLE 1

| Solvent | Solvent amount | Reaction time (hours) | OXN yield |
|---|---|---|---|
| Tetrahydrofuran | 80 ml | 5 | 85% |
| Toluene | 60 ml | 5 | 31% |
| tert.Butyl methyl ether | 80 ml | 5 | 46% |
| Acetonitrile | 60 ml | 4 | 95% |
| N-Methylpyrrolidone | 80 ml | 2 | 96% |

These results show that acetonitrile or N-methylpyrrolidone is especially preferred for the dehydration of OXA to OXN.

b) Use of different bases

These experiments were carried out at 60° C. with 60 ml of acetonitrile as the solvent and 4.4 g (26 mmol) of $SiCl_4$ as the dehydrating agent ($SiCl_4$:OXA molar ratio=1.3:1). The reaction time lay in the region of 3.5–5.5 hours. The results of the experiments in which different bases were used in an amount of 60 mmol, e.g. 6.07 g of triethylamine or 11.1 g of tri(n-butyl)amine, are compiled in the following Table 2. The yields of OXN were determined by GC.

TABLE 2

| Base | Reaction time (hours) | OXN yield |
|---|---|---|
| Triethylamine | 4 | 95% |
| Tri(n-butyl)amine | 3.5 | 94% |
| Pyridine | 5 | 90% |
| Quinoline | 5.5 | 94% |

The results show that good yields of OXN were achieved with the use of the above aliphatic and aromatic tertiary amines.

c) Use of different molar ratios

These experiments were carried out at 60° C. with 80 ml of tetrahydrofuran as the solvent and 6.07 g (60 mmol) of triethylamine as the base, with the reaction time being 5 or 16 hours. The results of the experiments in which different $SiCl_4$:OXA molar ratios and in each case 2.25 g (20 mmol) of OXA were used are compiled in the following Table 3. The yields of OXN were determined by GC.

TABLE 3

| Molar ratio $SiCl_4$:OXA | Reaction time (hours) | OXN yield |
|---|---|---|
| 3:1 | 5 | 92.5% |
| 1.5:1 | 16 | 94.5% |
| 1.3:1 | 5 | 85.0% |
| 1.1:1 | 5 | 84.5% |

The results show that, for the dehydration of OXA, an excess of $SiCl_4$ is required, which is due to the influence of the solvent (tetrahydrofuran in this case).

EXAMPLE 2

These experiments were carried out analogously to the procedure described in Example 1, but starting from 63.1 g (0.5 mol) of OXA and using different amounts of tri(n-butyl) amine base, acetonitrile solvent and $SiCl_4$ dehydrating agent. Further, the reaction time was varied. All experiments were carried out at 55° C. The results of the experiments are compiled in the following Table 4. The yields of OXN were determined by GC. The details relating to the amounts of base and $SiCl_4$ are given in equivalents based on the amount of OXA used.

TABLE 4

| Amount of Base (eq.) | Amount of $SiCl_4$ (eq.) | Amount of solvent (ml) | Reaction time (hours) | OXN yield |
|---|---|---|---|---|
| 2.1 | 0.7 | 85 | 6 | 88 |
| 2.8 | 0.7 | 85 | 6 | 87 |
| 2.8 | 0.7 | 170 | 5 | 89 |
| 2.8 | 0.735* | 170 | 5.5 | 89 |
| 2.8 | 0.735* | 285 | 8 | 95 |

*The amount of $SiCl_4$ was added in portions of 0.7 and 0.035 equivalents.

EXAMPLE 3

63.1 g (0.5 mol, dried, with a maximum water content with 0.2%) of OXA were placed under argon in a 21 four-necked round flask fitted with a stirrer, thermometer, 100 ml dropping funnel (without pressure balance), three-way stopcock for inert gasification and Dimroth condenser. Subsequently, 285 ml (222.9 g, 5.43 mol) of acetonitrile and 350.2 ml (272.1 g, 1.47 mol) of tri(n-butyl) amine were added. The resulting suspension was stirred at 25° C. for 5 minutes and subsequently 40 ml (59.3 g, 0.35 mol) of $SiCl_4$ were added dropwise from a dropping funnel within one hour in such a manner that the internal temperature in the flask did not rise above 45° C. After the addition of the $SiCl_4$ the batch became reddish in colour. The reaction mixture was then heated to 55° C. in an oil bath, during which the content of the flask became dark in colour. The formation of OXN was determined directly from the batch by means of GC and addition of an internal standard ($C_{11}$-alkane).

After a reaction period of 2.5 hours an equilibrium of 79% OXN and 15% OXA became established (about 6% of the expected total amount were not recorded). In order to increase the yield of OXN, an additional 2.2 ml (3.25 g, 19.6 mmol) of undiluted $SiCl_4$ were added dropwise to the batch within 10 minutes, so that the total amount of $SiCl_4$ was then 62.55 g (0.369 mol, i.e. 0.738 eq. $SiCl_4$ based on OXA). After a total reaction period of 5.5 hours about 89.4% OXN and 4.4% OXA (about 6.2% not registered) were established. After a total reaction period of 6.5 hours the reaction solution was cooled to 25° C. and worked-up as described hereinafter:

4.21 ml (0.234 mol) of deionized water were added dropwise while stirring, with the temperature of the reaction solution rising to about 45° C. After 15 minutes the mixture was cooled to 25° C. After removing the Dimroth condenser and replacing the dropping funnel by a distillation bridge all distillable substances (acetonitrile solvent, OXN, tri(n-butyl)amine base and any small amounts of tri(n-butyl) amine hydrochloride) were flash distilled.

The total amount of distillate was 291.1 g (theory: 272 g from 223 g of acetonitrile and 49 g of OXN).

For the working-up and isolation of the tri(n-butyl-amine hydrochloride, 237.3 ml of 28% sodium hydroxide solution (2.202 mol of NaOH based on the amount of $SiCl_4$) were added dropwise to the distillation residue at an oil bath temperature of 90° C. within 15 minutes without stirring. A clear solution formed after about 60 minutes. The contents of the flask were cooled to 25° C. and thereafter transferred into a 21 separating funnel, with rinsing being carried out with 60 ml of deionized water. A rapid phase separation took place in the separating funnel. 228 g of crude tri(n-butyl) amine were obtained as a clear red-brown coloured product. The aqueous phase was back-extracted three times with 60 ml of tert.butyl methyl ether each time. The ether phases were combined and concentrated under reduced pressure (about 400 mbar) at a bath temperature of 40° C. About 1 g of crude tri(n-butyl)amine was obtained.

Silicon dioxide was precipitated as a solid, almost colourless precipitate by adjusting the pH value to 6.3. Subsequently, this precipitate was separated by filtration and dried to constant weight.

We claim:

1. A process for the manufacture of a 5-cyano-4-lower alkyl-oxazole which comprises reacting, in an aprotic organic solvent, a 5-carbamoyl-4-lower alkyl-oxazole with silicon tetrachloride in the presence of an amine, to dehydrate said 5-carbamoyl-4-lower alkyl-oxazole and thereby produce said 5-cyano-4-lower alkyl-oxazole.

2. The process according to claim 1 wherein the silicon tetrachloride:5-carbamoyl-4-lower alkyl oxazole molar ratio is from about 0.6:1 to about 3:1, the amine:5-carbamoyl-4-lower alkyl-oxazole molar ratio is from about 2.1:1 to about 3.5:1, and the aprotic organic solvent is present in an amount from about 500 ml to about 900 ml per mole of oxazole.

3. The process of claim 2 wherein the lower alkyl group is methyl or ethyl.

4. The process of claim 3 wherein the amine is an aliphatic amine or a nitrogen-containing heteroaromatic compound.

5. The process of claim 4 wherein the amine is a trialkylamine in which the alkyl groups each contain 1 to 10 carbon atoms.

6. The process of claim 5 wherein the trialkylamine is triethylamine, diisopropylethylamine or tri(n-butyl)amine.

7. The process of claim 6 wherein the lower alkyl group is methyl.

8. The process of claim 7 wherein the aprotic organic solvent is an aliphatic or cyclic ether, an aliphatic nitrile, an aromatic hydrocarbon or N-methylpyrrolidone.

9. The process of claim 8 wherein the aprotic organic solvent is tert.butyl methyl ether or acetonitrile.

10. The process according to claim 9 wherein the silicon tetrachloride:5-carbamoyl-4-lower alkyl oxazole molar ratio is from about 0.7:1 to about 0.75:1, the amine:5-carbamoyl-4-lower alkyl-oxazole molar ratio is from about 2.7:1 to about 2.9:1, and the aprotic organic solvent is present in an amount from about 550 ml to about 650 ml per mole of oxazole.

11. The process of claim 10 wherein the reaction is carried out at a temperature in the range from room temperature to about 65° C.

12. The process of claim 11 wherein the reaction is carried out at a temperature in the range from about 25° C. to about 60° C.

13. The process of claim 12 wherein the reaction is carried out at a temperature in the range from about 45° C. to about 55° C.

14. The process of claim 4 wherein the amine is pyridine or a pyridine derivative.

15. The process of claim 14 wherein the lower alkyl group is methyl.

16. The process of claim 15 wherein the aprotic organic solvent is an aliphatic or cyclic ether, an aliphatic nitrile, an aromatic hydrocarbon or N-methylpyrrolidone.

17. The process of claim 16 wherein the aprotic organic solvent is tert.butyl methyl ether or acetonitrile.

18. The process according to claim 17 wherein the silicon tetrachloride:5-carbamoyl-4-lower alkyl oxazole molar ratio is from about 0.7:1 to about 0.75:1 the amine:5-carbamoyl-4-lower alkyl-oxazole molar ratio is from about 2.7:1 to about 2.9:1, and the aprotic organic solvent is present in an amount from about 550 ml to about 650 ml per mole of oxazole.

19. The process of claim 18 wherein the reaction is carried out at a temperature in the range from room temperature to about 65° C.

20. The process of claim 19 wherein the reaction is carried out at a temperature in the range from about 25° C. to about 60° C.

21. The process of claim 20 wherein the reaction is carried out at a temperature in the range from about 45° C. to about 55° C.

* * * * *